US009592378B2

(12) United States Patent
Gluckman et al.

(10) Patent No.: US 9,592,378 B2
(45) Date of Patent: Mar. 14, 2017

(54) MICRO-REACTION CHAMBER MICROELECTRODES ESPECIALLY FOR NEURAL AND BIOINTERFACES

(75) Inventors: Bruce J. Gluckman, State College, PA (US); Balaji Shanmugasundaram, State College, PA (US)

(73) Assignee: THE PENN STATE RESEARCH FOUNDATION, University Park, PA (US)

(*) Notice: Subject to any disclaimer, the term of this patent is extended or adjusted under 35 U.S.C. 154(b) by 1087 days.

(21) Appl. No.: 13/595,656

(22) Filed: Aug. 27, 2012

(65) Prior Publication Data
US 2013/0053934 A1 Feb. 28, 2013

Related U.S. Application Data

(60) Provisional application No. 61/528,268, filed on Aug. 28, 2011.

(51) Int. Cl.
A61N 1/05 (2006.01)
C25F 3/02 (2006.01)
A61B 5/00 (2006.01)
A61B 5/04 (2006.01)

(52) U.S. Cl.
CPC ........ A61N 1/0551 (2013.01); *A61B 5/04001* (2013.01); *A61B 5/6877* (2013.01)

(58) Field of Classification Search
CPC A61N 1/0551; A61B 5/6877; A61B 5/04001; C25B 11/00
See application file for complete search history.

(56) References Cited

U.S. PATENT DOCUMENTS 7,899,552 B2    3/2011  Atanasoska et al.
2008/0319298 A1* 12/2008  Huys ............... G01N 33/48728
                                                            600/377

OTHER PUBLICATIONS

Cogan, Stuart F. et al., "Sputtered iridium oxide films (SIROFs) for neural stimulation electrodes", Proceedings of the 26th Annual International Conference of the IEEE EMBS, 2004, pp. 4153-4156.
Snow, Sean et al., "Microfabricated Cylindrical Multielectrodes for Neural Stimulation", IEEE Transactions on Biomedical Engineering, 2006, vol. 53(2), pp. 320-326.
The Penn State Research Foundation, PCT/US2012/052515 filed Aug. 27, 2012, "International Search Report and Written Opinion of the International Searching Authority", mailed Oct. 22, 2012, 7 pages.
Abidian, Mohammad Reza et al., "Conducting-Polymer Nanotubes Improve Electrical Properties, Mechanical Adhesion, Neural Attachment, and Neurite Outgrowth of Neural Electrodes", Small 2010, 6, No. 3, 421-429.

(Continued)

*Primary Examiner* — Gurpreet Kaur
(74) *Attorney, Agent, or Firm* — McKee, Voorhees & Sease, PLC

(57) ABSTRACT

Biocompatible electrodes with smaller geometric area improve the selectivity of the neural recording and stimulation applications. A volume within the electrode back plane of a micro-reaction chamber (μRC) is used to confine and sequester an electrochemical reaction used for charge passage. The μRC electrode decreases impedance and improves charge storage capacity without altering the geometry of the active site.

22 Claims, 15 Drawing Sheets

(a)  (b)  (c)

(56) References Cited

OTHER PUBLICATIONS

ASTM International, Designation: B 912-02 (Reapproved 2008), "Standard Specification for Passivation of Stainless Steels Using Electropolishing" 4 pg.
BMES "Poster Session 10A" Oct. 10, 2009.
Desai, Sharanya Arcot et al., "Improving impedance of implantable microwire multi-electrode arrays by ultrasonic electroplating of durable platinum black", Frontiers in Neuroengineering, May 2010, vol. 3, Article 5. pp. 1-11.
Kim, Dong-Hwan et al., "Conducting polymers on hydrogel-coated neural electrode provide sensitive neural recordings in auditory cortex", Acta Biomaterialia 6 (2010) 57-62.
Merrill, Daniel R. et al., "Electrical stimulation of excitable tissue: design of efficacious and safe protocols", Journal of Neuroscience Methods 141 (2005) 171-198.
Meyer, Ross D. et al., "Electrodeposited Iridium Oxide for Neural Stimulation and Recording Electrodes", IEEE Transactions on Neural Systems and Rehabilitation engineering, vol. 9, No. 1, Mar. 2001.
Shanmugasundaram, Balaji et al., "In Vitro and In Vivo Performance of Novel Neural Electrodes", PennState.
Shanmugasundaram, Balaji et al., "Thin Film Coatings with High Charge Passing Capacity for Neural Electrodes", Abstract.
Yang, Junyan et al., "Microporous conducting polymers on neural microelectrode arrays I Electrochemical deposition", Sensors and Actuators B 101 (2004) 133-142.

\* cited by examiner

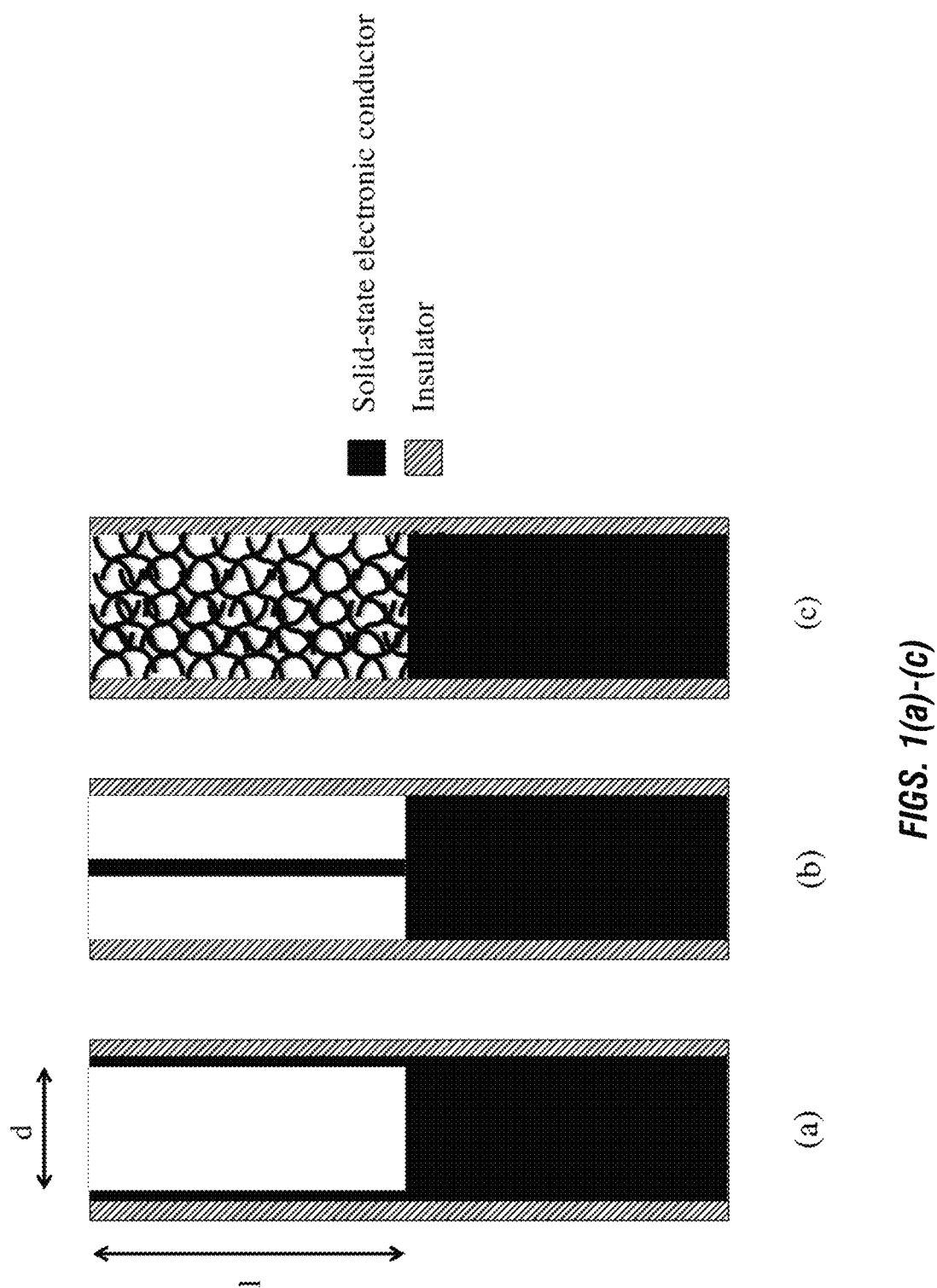
FIGS. 1(a)-(c)

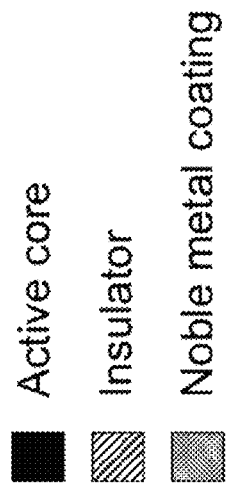
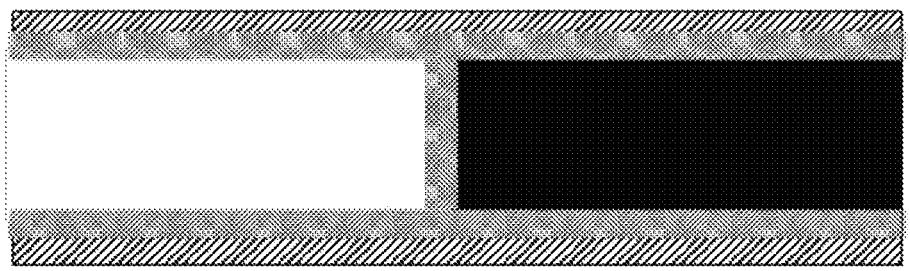
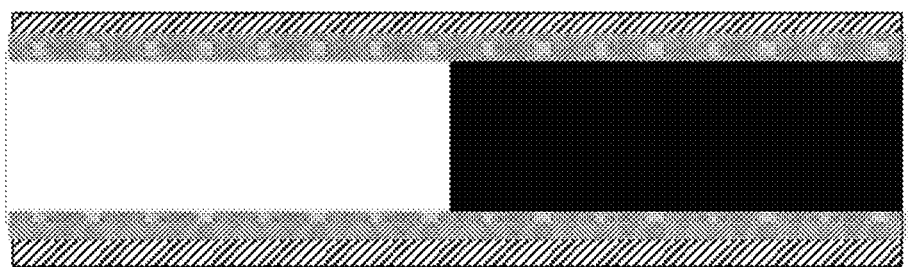
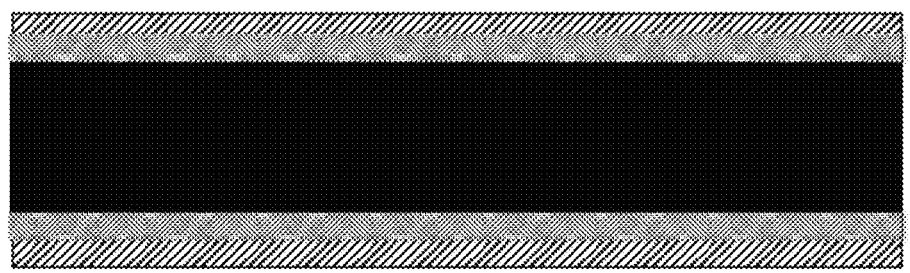
FIGS. 2(a)-(c)

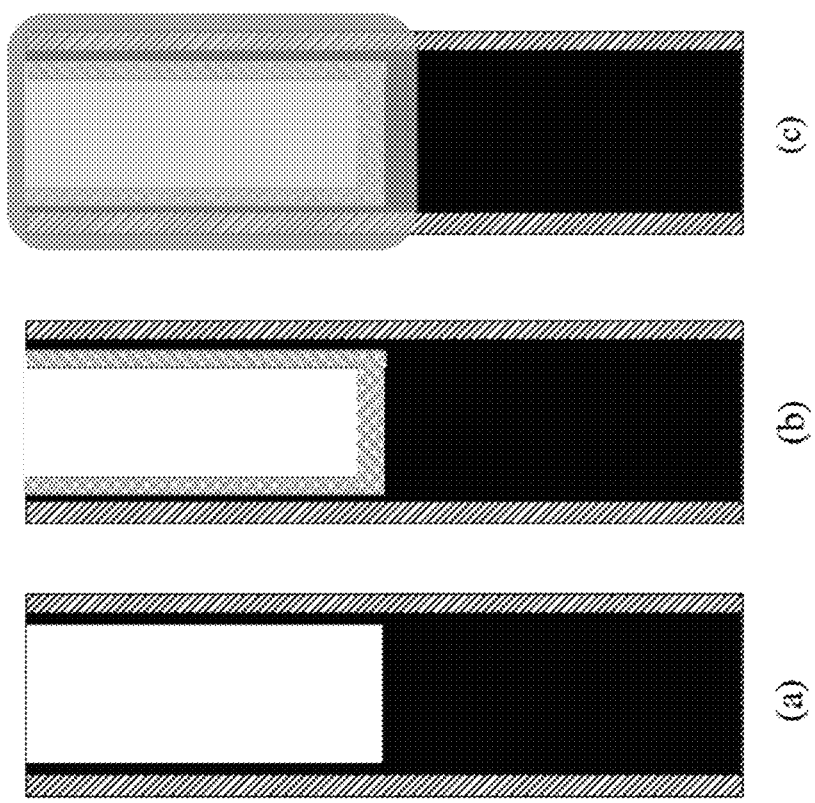
FIGS. 4(a)-(c)

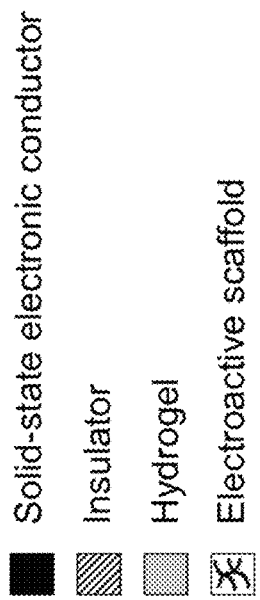
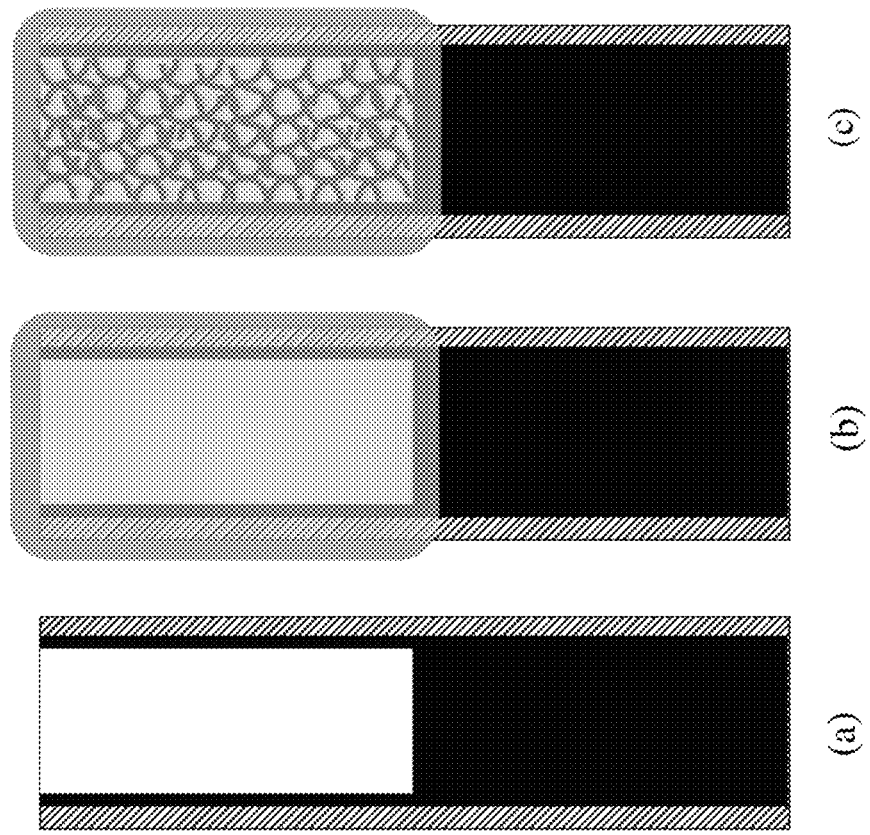
FIGS. 5(a)-(c)

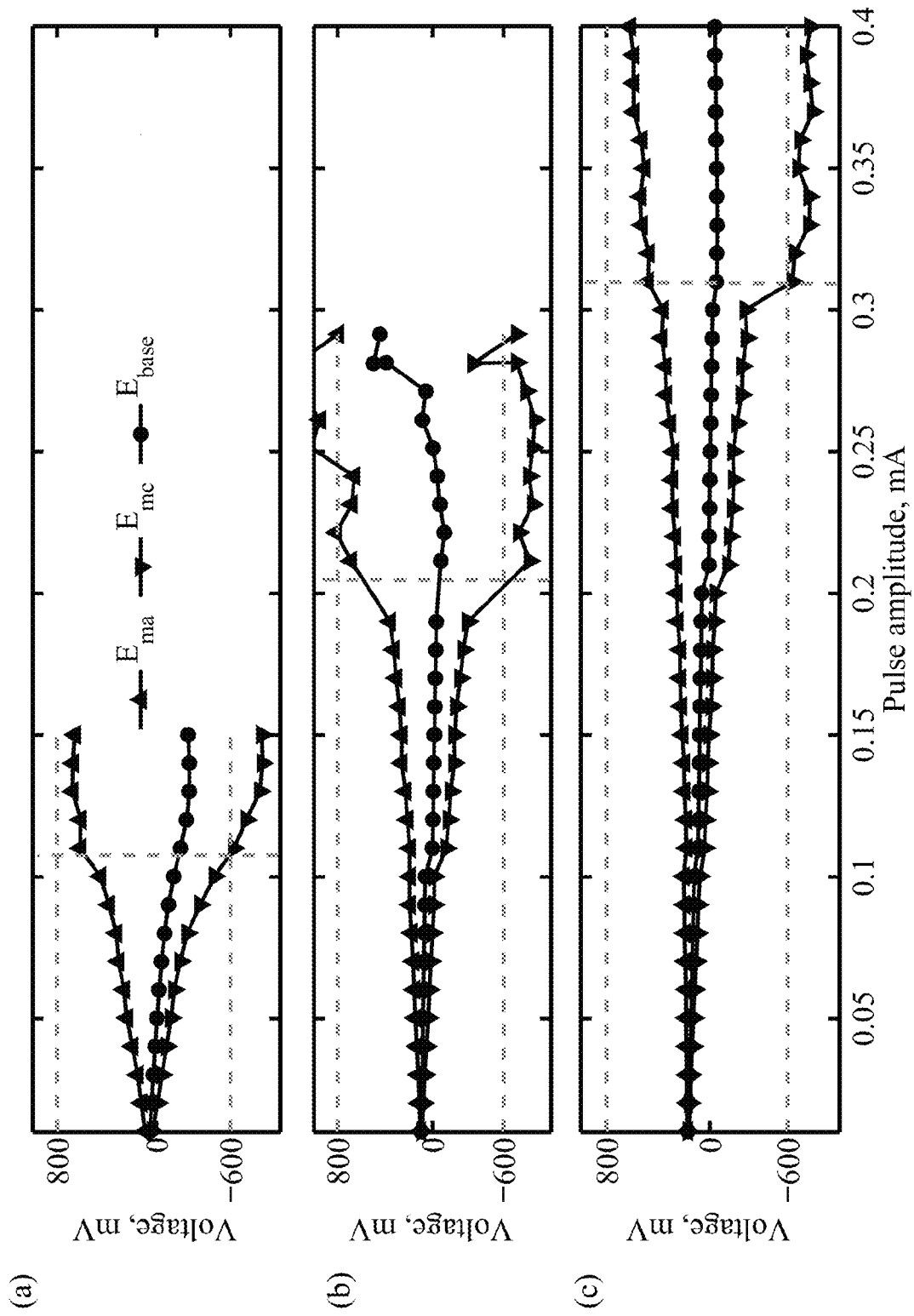
FIGS. 13(a)-(c)

MICRO-REACTION CHAMBER MICROELECTRODES ESPECIALLY FOR NEURAL AND BIOINTERFACES

CROSS-REFERENCE TO RELATED APPLICATIONS

This application claims priority under 35 U.S.C. §119 of a provisional application Ser. No. 61/528,268 filed Aug. 28, 2011, and which application is hereby incorporated by reference in its entirety.

GRANT REFERENCE

This invention was made with government support under Grant No. NS065096 awarded by the National institutes of Health. The government has certain rights in the invention.

BACKGROUND OF THE INVENTION

Field of the Invention

This invention relates generally to micro-reaction chamber electrodes and more particularly to micro-reaction chamber electrodes for neural stimulation and recording.

Description of the Prior Art

A major challenge for electrical interface to biological systems, especially neural interfaces, is that charge passing in biological tissue is through ions, whereas in electronic instrumentation is through electrons. Therefore, interfaces between instrumentation and tissue are limited by their ability to exchange charge. This is typically done through combinations of capacitance charge build-up and electrochemical reactions.

In general, electrochemistry deals with the processes that take place at the interface between the electronic conductor (electrode surface) and the ionic conductor (electrolyte). Electrochemical activity and hence the impedance of a particular electrode is restricted to the active area that is in contact with the electrolyte. Generally, only those materials at the exposed surface take part in the electrochemical processes making the underlying bulk substrate less important in charge passing as long as the surface coating is intact and defect free. Electrolyte-based electrochemical reactants and reaction products can undergo subsequent reactions in the bulk that affect both charge passing efficacy as well as safety.

In the case of neural interfaces, successful neural prosthesis requires efficient communication to and from central and/or peripheral nervous systems. Neural recording and stimulation electrodes act as transducers that mediate signal transport between the ionic tissue environment and the solid-state electronic environment of the prosthetic device. Electrodes of smaller geometry are generally preferred to improve the spatial locality and to decrease the tissue damage resulting from insertion trauma. This, however, leads to increase in interfacial impedance and increase in the required charge transfer density for a given stimulation pulse. Since charge transfer takes place at the electrode-tissue interface by either Faradaic or capacitive mechanisms, the two-dimensional interfacial area, also called the electrochemical surface area (ESA), determines the electrochemical activity of the electrodes. For an electrode with a given geometric surface area (GSA), improving the surface roughness either by etching the surface or by depositing porous coatings on the surface such as Pt black, iridium oxide, or conductive polymer helps increase ESA and enhance electrochemical activity of the electrodes. Modifying the surface morphology of the surface coating using micro and nanoscale templates to introduce pores has also resulted in significant increase in ESA. However, the useful thickness of these coatings is limited by the chemical transport inside the pores and the possibility of fragile surface coatings, cracking or delaminating under mechanical stress in situ.

It is therefore desirable to provide a solution to the electrochemical charge transfer limitation problem, and related reaction-product tissue damage, associated with current electrode designs.

It is further desirable to provide a micro-reaction chamber electrode having impedance that can approach that of an ideal, geometrically defined electrode independent of capacitive or Faradic effects.

It is further desirable to provide a micro-reaction chamber electrode having minimal electrode impedance, maximum charge passing capacity, improved reversibility, decreased tissue damage, and a longer operational life.

SUMMARY OF THE INVENTION

In one embodiment, the invention is a method for making highly localized low-impedance connections with an ionic conductive environment. The method includes providing an electrode having a reaction chamber with an electrochemical transfer interface at least partially enclosed by an insulating layer and an open end terminating in an electrode interface in communication with the reaction chamber. The method also includes connecting the electrode interface to tissue within the ionic conductive environment and spatially separating the electrode interface from the electrochemical transfer interface with the reaction chamber for increasing charge passing capacity and decreasing impedance. In a preferred form, the electrochemical transfer interface (ETI) is distributed to be geometrically close to all positions in the bulk of the chamber and to have high surface to volume ratio. In a preferred form, the method also includes improving the electrochemical transfer capacity at the ETI by coating with one or more electroactive species such as iridium oxide and/or conductive polymer. The ETI can be further extended through the chamber by growing it as a scaffold, for example by depositing through a polymer network such as sodium alginate hydrogel. The reaction chamber can also be filled with a biocompatible dissolvable material to stiffen it during implantation.

In another embodiment, the invention is a method for manufacture of micro-reaction chamber electrodes. The method includes providing a mostly enclosed chamber volume terminating in an opening and having a high surface to volume ratio. An electrochemical transfer interface is distributed throughout the chamber volume to maximize the surface area of the electrochemical transfer interface with respect to the chamber volume. A conductor is also provided that is in charge carrying communication with the chamber volume via the electrochemical transfer interface. In a preferred form, the electrochemical transfer interface is coated with one or more electroactive species. Optionally, the electrochemical transfer interface may be extended into the chamber volume by one or more conductive threads or fibers, a conductive mesh or scaffolding, and by depositing through a polymer.

In another embodiment, the invention is a micro-reaction chamber electrode. The micro-reaction chamber electrode includes a mostly enclosed chamber volume terminating in an opening and having a high surface to volume ratio, an electrochemical transfer interface distributed throughout the chamber volume to maximize the surface area of the electrochemical transfer interface with respect to the chamber volume, and a conductor in charge carrying communication with the chamber volume via the electrochemical transfer interface. In a preferred form, the micro-reaction chamber electrode includes an electroactive species covering the inner surface of the chamber volume to increase its charge passing capacity. Optionally, a conductor may be configured to extend into the chamber volume to extend the electrochemical transfer interface.

BRIEF DESCRIPTION OF THE DRAWINGS

FIGS. 1(a)-(c) are exemplary illustrations of various embodiments for different reaction chamber electrochemical transfer interface geometries of the present invention.

FIGS. 2(a)-(c) are exemplary illustrations of a fabrication process for microwire based micro-reaction chamber electrodes of the present invention.

FIGS. 4(a)-(c) are additional exemplary illustrations of the fabrication process for microwire based micro-reaction chamber electrodes shown in FIGS. 2(a)-(c).

FIGS. 5(a)-(c) are additional exemplary illustrations of the fabrication process for microwire based micro-reaction chamber electrodes shown in FIGS. 2(a)-(c) and 3(a)-(c).

FIGS. 13(a)-(c) are plots of electrode polarization voltages versus pulse amplitude for an electrodeposited iridium oxide (EIROF) SPl electrode shown in FIG. 13(a) and an electrodeposited iridium oxide (EIROF) micro-reaction chamber electrode at 5 minutes electrodissolution shown in FIG. 13(b) and 10 minutes electrodissolution shown in FIG. 13(c).

DETAILED DESCRIPTION OF THE PREFERRED EMBODIMENTS

FIGS. 1(a)-(c), 2(a)-(c), and 4(a)-(c) illustrate exemplary embodiments of micro-reaction chambers (μRC) of the present invention in which a volume within the electrode back plane is used to confine and sequester the electrochemical reactions that are involved in charge passage. The connection from the μRC to the tissue is an opening that replaces the geometric surface of a classical electrode. In μRC electrodes, the area of the electrode back plane replaces the two-dimensional ESA of the solid-planar (SPl) electrode for charge exchange, offering much higher electroactivity for the given GSA. Hence, μRC electrodes improve sensitivity without impairing selectivity. Also, the sequestering of the electrochemical reaction products within the microchamber help enhance the reversibility of the charge transfer reactions and improving charge transfer safety. Further when implanted in the neural tissue, the reactive coatings are protected from the insertion related damages and tissue inflammatory reactions as they are encapsulated within the reaction-chambers.

FIGS. 1(a)-(c), 2(a)-(c), and 4(a)-(c) illustrate basic designs of μRC electrodes according to embodiments contemplated by the present invention. The complete volume of the hollow region within the inner diameter (d) and length (l) is defined as the micro-reaction chamber (see FIG. 1(a)). The outer insulation restricts the electrical axis only through the opening at the tip and helps maintain the same geometric surface area (GSA) as that of other reference or solid-planar electrodes. For an electrode with circular cross section, the μRC electrode achieves (1+4(l)/(d)) times larger effective GSA (EGSA) than SPl electrodes. Different reaction chamber electrochemical transfer interface (ETI) geometries are shown in FIGS. 1(a)-(c). The charge transfer from the solid-state conductor to the electrolyte occurs at the interface between the conductor and the electrolyte within the chamber. Charge transfer should be optimized by maximizing the surface area of the ETI with respect to the volume of the chamber, as well as minimizing the distance between points in the bulk of the chamber and the nearest ETI so that they are small with respect to the inner dimension (d) of the opening. Three potential—and readily fabricated—geometries for the ETI include coating the walls of the chamber as shown in FIG. 1(a), utilizing one or more conductive threads or fibers that extend through the chamber as shown in FIG. 1(b), and utilizing a mesh or scaffold of conductor through the volume as shown in FIG. 1(c). Although FIGS. 1(a)-(c) provide illustrations of varying ETI geometries, the present invention contemplates other ETI geometries. For example, any geometry that maximizes the surface area of the ETI relative to the volume of the chamber is desirable.

Figure 3A:
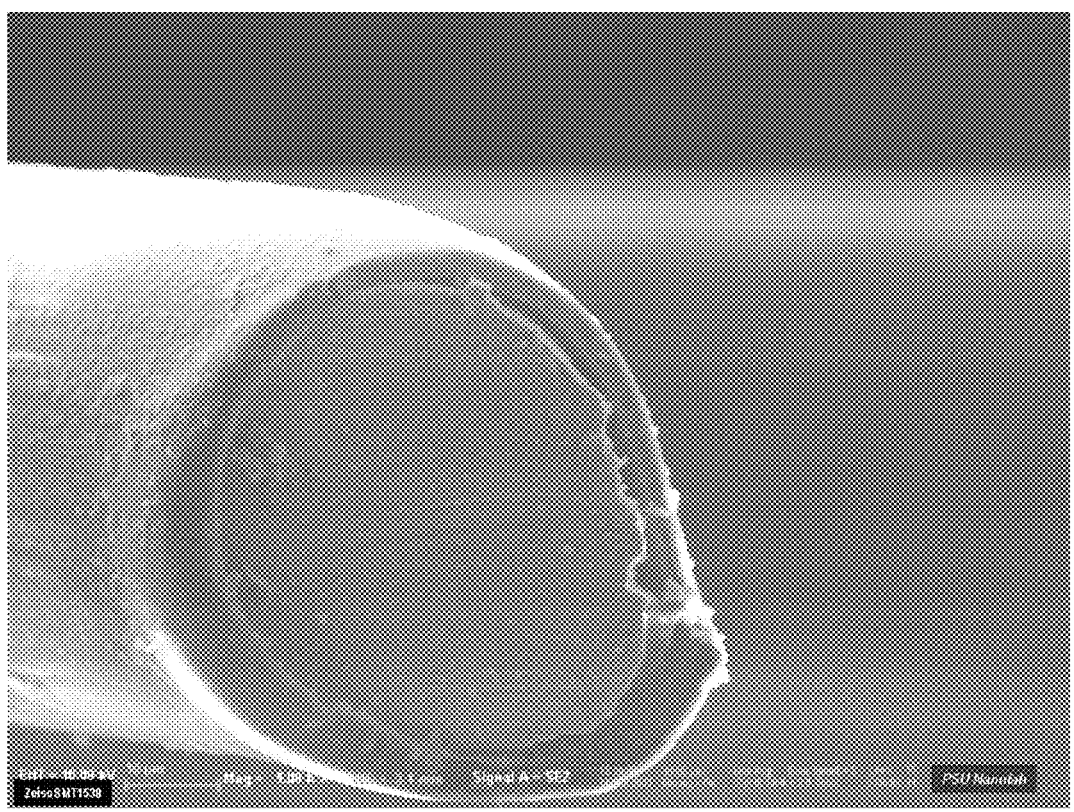
FIGS. 3(a)-(c) are SEM images of each stage represented in the fabrication process shown in FIGS. 2(a)-(c).
Figure 3B:
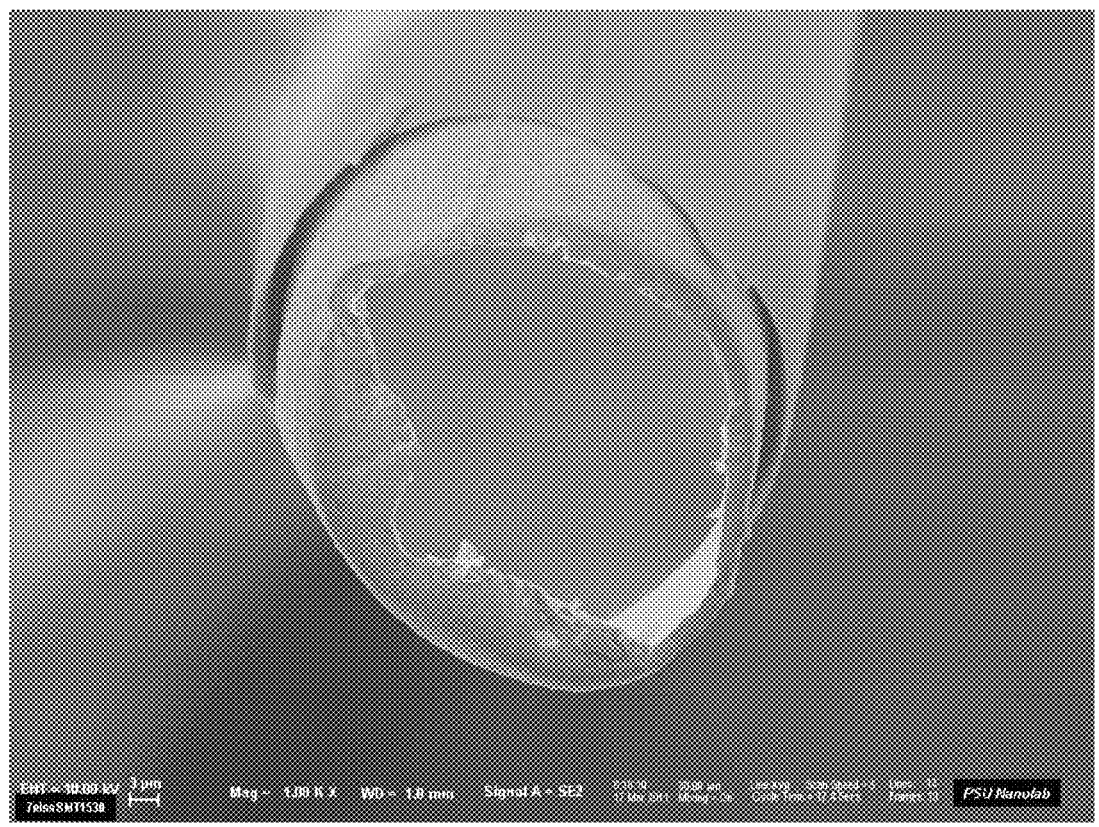
Figure 3C:
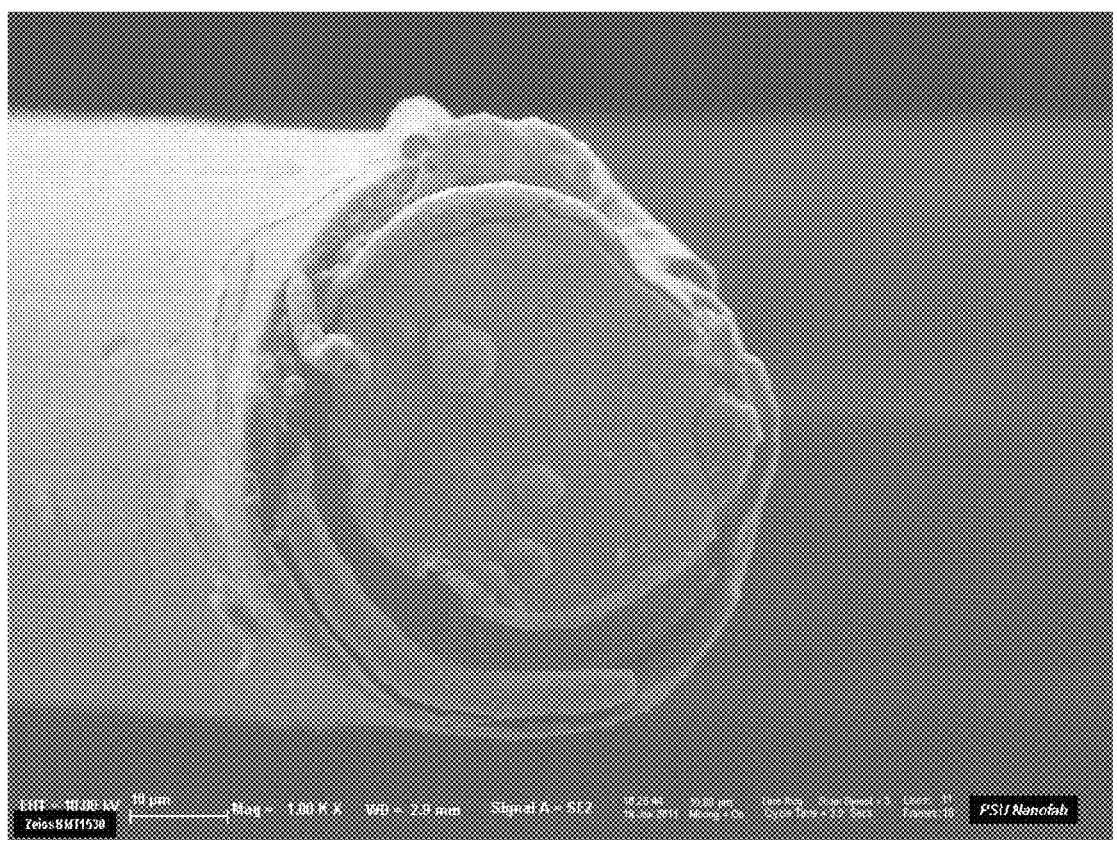

A fabrication process for preparing μRC electrodes according to a general aspect of the present invention is shown in FIGS. 2(a)-(c) and FIGS. 4(a)-(c). According to one fabrication process, a base stock of wire comprised of an active core, coated with a noble metal coating and insulated on the outside or cleaved on one end may be used (see FIG. 2(a)). An SEM image of a microwire corresponding to the schematics shown in FIG. 2(a) is shown in FIG. 3(a). A dissolution process is used to dissolve the active core to form a reaction chamber as shown in FIG. 2(b). An SEM image of the microwire after electrodissolution is shown in FIG. 3(b). The depth of the reaction chamber may be controlled by adjusting the duration of the electrodissolution process. Next the active core within the reaction chamber is encapsulated with a noble metal as shown in FIG. 2(c). After creating the reaction chamber, the walls of the chamber, which form the electrochemical transfer interface (ETI), may be coated with an electroactive coating as shown in FIG. 4(b) to improve charge passage from the solid-state electronic conductor to the electrolyte solution. An SEM image of the electroactive coating is shown in FIG. 3(c). The reaction chamber can also then be filled and/or coated with a polymer hydrogel to improve biocompatibility as shown in FIG. 4(c) and/or a dissolvable coating to provide structural support during insertion. For example, filling the tube with the hydrogel, as shown by illustration in FIGS. 4(c) & 5(b), will provide stiffness for insertion through a jelly-like electrochemical environment, such as brain tissue, and provide a conductive channel for ionic transport between an electrode and electrolyte. Growing electroactive materials (e.g., conductive polymer/iridium oxide) through the sparse hydrogels of electrode scheme shown by illustration in FIG. 5(b) can help reduce the impedance and result in electrode illustrated in FIG. 5(c). The electroactive scaffold shown in FIG. 5(c) is deposited to act as the electrochemical transfer interface (ETI). The inner surface of the conductive tube can be coated with an electroactive coating or film, such as iridium oxide or conductive polymers as discussed above and further shown by illustration in FIG. 4(b). The inner surface of the conductive tube may also be filled with hydrogels to form the scheme illustrated in FIG. 4(c). The reaction chamber ETI may also be deposited with a multilayer stack of electroactive species, for example a combination of electrodeposited iridium oxide and conductive polymer, which increases the electroactivity of the electrode as discussed above.

Figure 6:
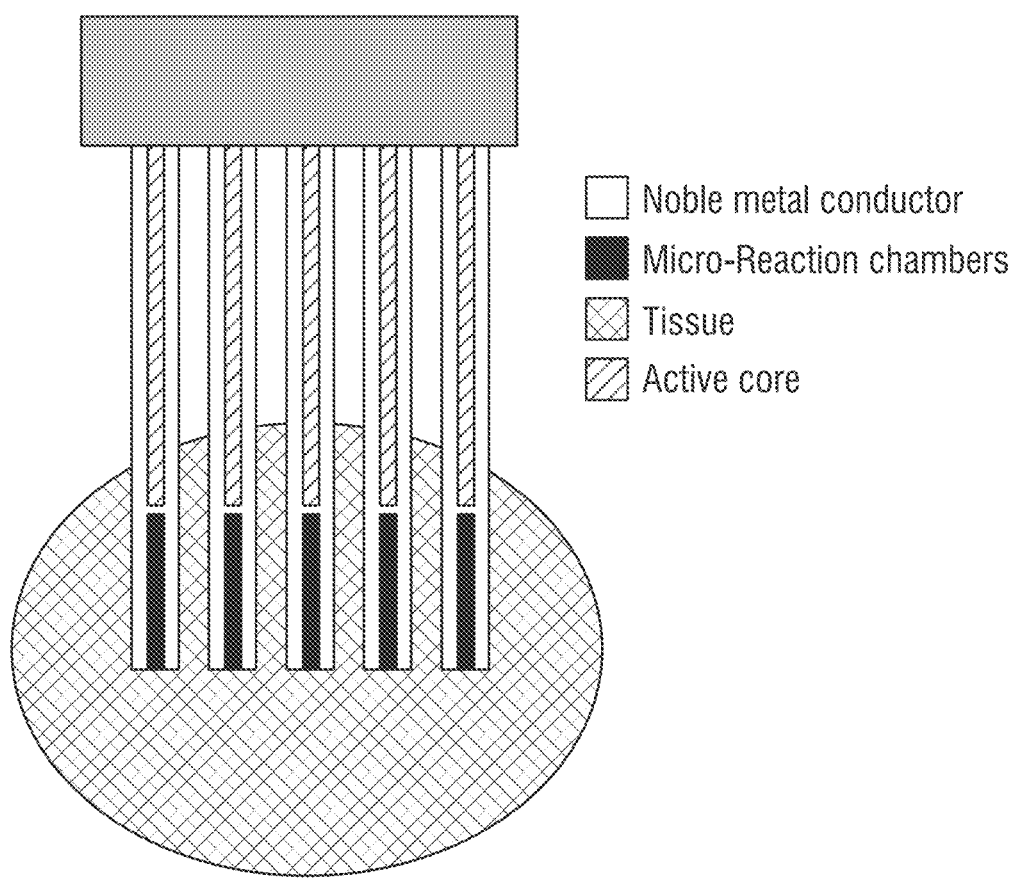
FIG. 6 is an illustration of an array of micro-reaction chamber electrodes fabricated in parallel according to one aspect of the present invention.
Figure 7:
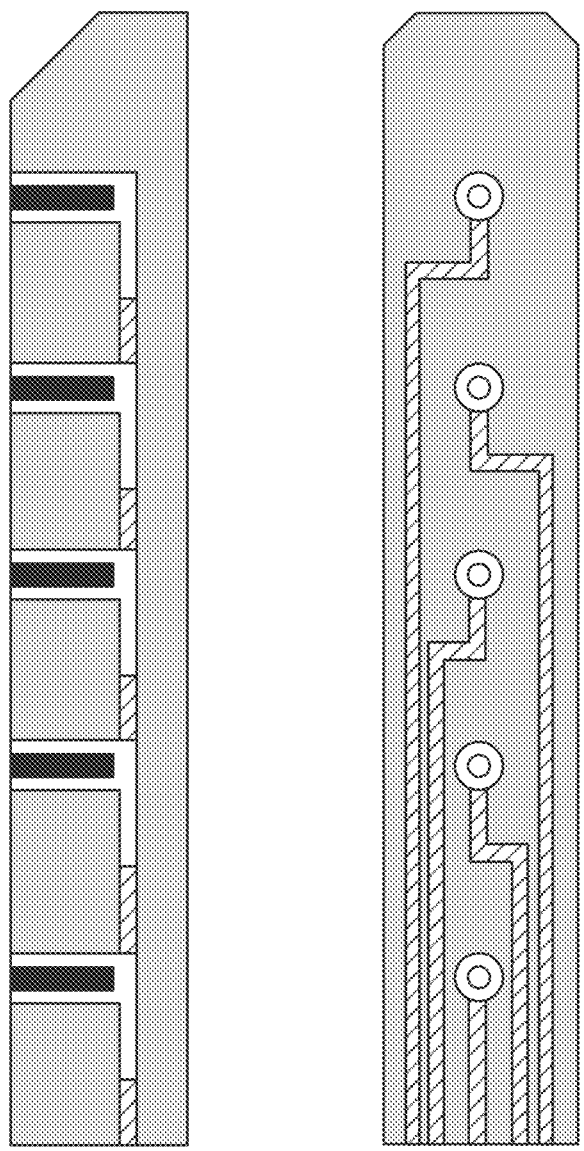
FIG. 7 is another illustration of an array of micro-reaction chamber electrodes fabricated in a base material according to one embodiment of the present invention.
Figure 8:
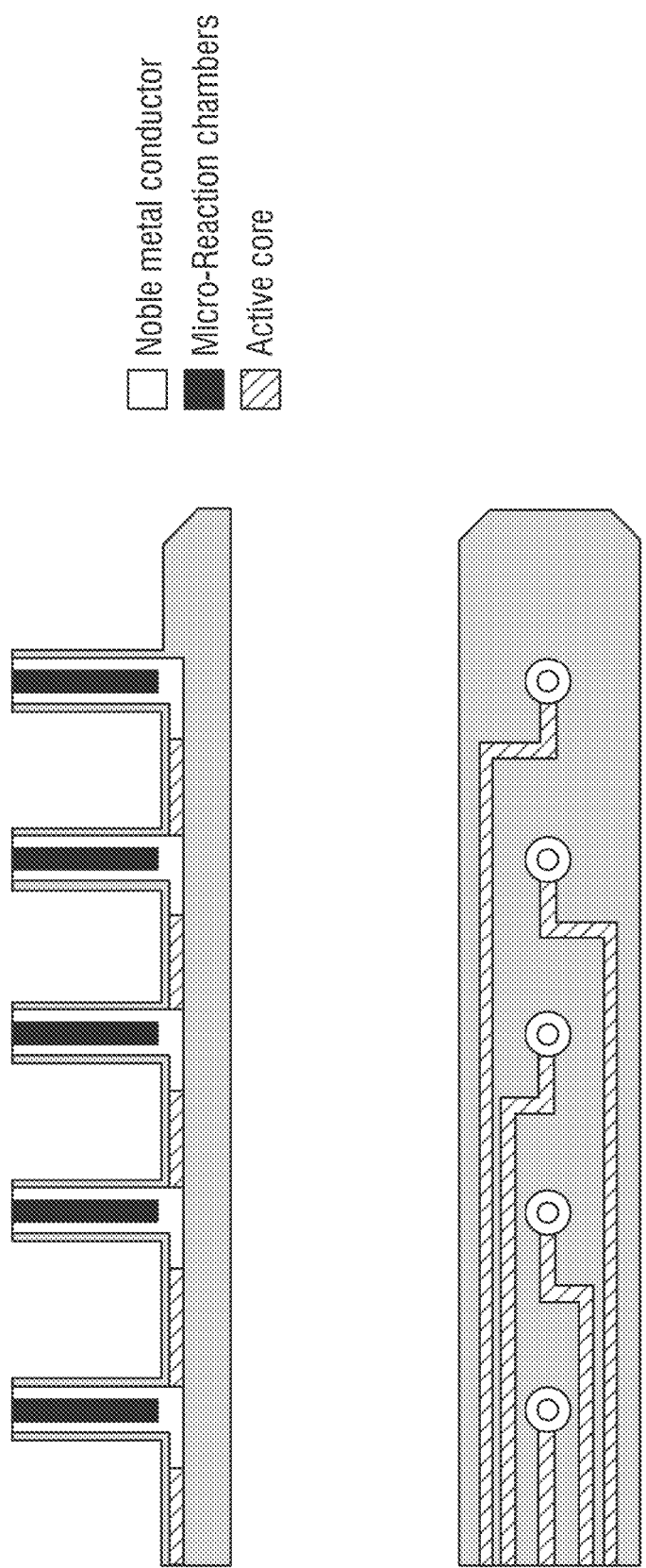
FIG. 8 is another illustration of an array of micro-reaction chamber electrode fabricated as protruding from a base material according to another embodiment of the present invention.

The present invention also contemplates the parallel fabrication of μRC electrodes configured as microwire arrays, such as the exemplary illustration provided in FIG. 6. These microwire arrays may be manufactured by processing similar geometry and material composition wires in parallel. Like the above embodiments, each microwire includes a mostly enclosed volume (i.e., micro-reaction chamber), a noble metal conductor and an ETI. The microwire also includes an active core. The array of microwires is brought into contact with an ionic environment, such as tissue. FIGS. 7-8 illustrate other exemplary embodiments of the micro-reaction chamber electrode of the present invention. The micro-reaction chamber electrode can be fabricated as part of a larger structure device using current or newer fabrication or microfabrication processes. For example, the micro-reaction chamber electrode could be fabricated as part of an array made with solid backings which contain electrical connections and/or active electronics formed from or on silicone, parylene, or polyimide. The micro-electrode arrays can then be formed as single elements or arrays from wells or tubes that are fabricated into the back plane, and have an opening to the ionic solution. In another exemplary aspect of the present invention, the micro-electrode arrays could take the form of tubes that are insulated from the outside, except at the physical opening at the terminal end of the reaction chamber that establishes the electro-connection with the ionic system of interest. The wells or tubes constitute the reaction chamber. Charge is electrochemically exchanged into the chamber through an ETI, which is formed from a solid-state conductive element. The conductive element forming the ETI could be gold, or another non-reactive (or minimally reactive) metal or nonmetal conductor, including platinum, iridium, conductive polymer, conductive composite materials, carbon fiber, carbon nanotubes (CNT), etc. The geometry of the ETI may be a tube formed from the inside walls of the chamber. Alternately, the ETI can be constructed from single or multiple conductive fibers within the chamber (see FIG. 1(b)) or a structured or unstructured mesh of conductor within the chamber (see FIG. 1(c)).

EXAMPLES

Embodiments of the present invention are further defined in the following non-limiting examples and in B. Shanmugasundaram and B. J. Gluckman, "Micro-reaction chamber electrodes for neural stimulation and recording" Proc. IEEE Eng. Med Biol. Soc. 2011, pp. 656-659 which is incorporated by reference herein in its entirety. It should be understood that this example, while indicating a certain embodiment of the invention, is given by way of illustration only. From the above discussion and this example, one skilled in the art can ascertain the essential characteristics of the invention, and without departing from the spirit and scope thereof, can make various changes and modifications of the embodiments in the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Electrode Fabrication

According to one method of fabrication, micro-reaction chamber electrodes were prepared from 50 μm diameter 316L stainless steel microwires plated with 1 μm thick gold and insulated with polyimide (Supplier: California Fire Wire Company, Grover Beach, Calif., USA). In one aspect, the tip of the electrode is cut flat using a razor blade, creating a terminal end generally perpendicular to the electrode. The schematic of the steps involved in the fabrication of the microwire based μRC electrode are shown in FIGS. 2(a)-(c), 3(a)-(c), and 4(a)-(c). Selective electrochemical dissolution of 316L leaves behind a hollow, tubular region that is insulated from the outside. The exposed 316L is electroplated with gold according to one embodiment of the invention. Then, this hollow region may be deposited in one aspect of the present invention with multilayered coatings that contain stacks of electrodeposited iridium oxide (EIROF) and electropolymerized poly(3,4-ethylenedioxythiophene) (PEDOT) conductive polymer. The multilayer stacks were incorporated to overcome some of the short falls of single-element PEDOT and EIROF coatings, such as limited useful thickness, delamination of thicker coatings, and limited performance in low-buffering solutions.

Electrodissolution

Selective electrochemical dissolution of 316L stainless steel from the gold plated microwire was accomplished in part using a protocol identified as the ASTM B912 standard. Although a gold plated electrode is used in fabrication of the micro-reaction chamber electrode, the present invention contemplates that other conductive elements may be used in place of the gold, such as another non-reactive (or minimally reactive) metal or nonmetal conductor, including platinum, iridium, conductive polymer, conductive composite materials, carbon fiber, carbon nanotubes (CNT), etc. According to one aspect of the present invention, a 1:1 mixture (v/v) of concentrated sulphuric acid-phosphoric acid electrolyte heated to 75° C. was used for selective electrochemical dissolution of the 316L stainless steel from the electrode. Using a galvanostatic circuit, a current density of 11 mA/mm$^2$ was applied between a Pt cathode and the gold plated 316L anode for 300 seconds. Longer electrochemical dissolution times (e.g., 600 seconds to 30 minutes) provide for larger reaction chambers. After electrode dissolution, the electrodes are dipped in a 20% (v/v) nitric acid at room temperature and rinsed thoroughly with deionized water.

Electrodeposition of Electroactive Coatings on the Electrochemical Transfer Interface FIGS. 1(a)-(c), 2(a)-(c), 3(a)-(c) and 4(a)-(c) illustrate the electrodeposition of iridium oxide. The iridium oxide electrodeposition solution (Solution A) may be prepared by dissolving 4 mM IrCl$_4$ hydrate in 40 mM oxalic acid solution. The pH of this solution may be adjusted to 10.4 by slowly adding 3 M K$_2$CO$_3$ buffer solution. The color of the solution changes from dark purple to pale green. The solution is allowed to sit quiescently in the dark for a minimum of one week at room temperature before electrodeposition. The oxidation state of Ir in the oxalate complex attains equilibrium during this period. Electrodeposition of the iridium oxide layer was carried out using a two-electrode cell potentiostat using a large surface area AgCl pellet as a counter electrode.

A PEDOT:PSS electropolymerization solution (Solution B) may be prepared by dissolving 0.01 M of EDOT monomer in a 0.1 M poly(sodium 4-styrene sulfonate) solution. Mixing the solution overnight ensure complete dissolution of the EDOT monomer. The PEDOT:PSS electropolymerization may be performed using a three-electrode cell potentiostat.

Stack coatings on SPl electrode and µRC electrode substrates may be applied in three states. For example, in stage I, using Solution A, iridium oxide is electrodeposited by applying a combination of potential cycling with 50 triangular waveforms between limits of 0.0 V and 0.55 V at 50 mV/s sweep rate followed by 1000 rectangular potential pulses between the same voltage limits with 0.5 s width in each limit between the substrate and a large area AgCl pellet at room temperature. In stage II, for example, the PEDOT:PSS conductive polymers potentiostatically electropolymerized from Solution B, at 0.9 V vs. SCE reference in a three-electrode cell for 60 seconds. A large area Pt pellet may serve as the counter electrode in this case. The top layer of iridium oxide is electrodeposited from Solution A in state III, by applying 1800 rectangular potential pulses between 0.0 V and 0.55 V limits with 0.5 s width in each limit against a large area AgCl pellet.

Characterization

The morphology of the electrodes was imaged in an LEO 1530 field emission scanning electron microscope (FE-SEM). According to one aspect of the present invention, the in vitro electrochemical characterizations were performed in a phosphate buffered saline solution. Electrochemical Impedance Spectroscopy (EIS) was recorded using an Autolab PGSTAT-12. An AC sinusoidal signal of 10 mV rms was used to record the impedance over a frequency range of 0.1-100000 Hz. The test electrodes are connected as working electrodes and a large area Pt foil served as a counter electrode. The saturated calomel electrodes were used as reference electrodes.

In vitro charge storage capacities (CSC) of the electrodes were measured by performing cyclic voltammetry at 50 mV/s sweep rate in between the voltage limits of –0.6 V and 0.8 V vs. SCE reference in a three electrode potentiostat. The test electrode was connected as a working electrode and a large area Pt pellet was used as a counter electrode. The CV of the first cycle is discarded and the second cycle is reported. The currents are normalized with respect to the GSA, which is the same for both solid-planar and µRC electrodes. Charge storage capacity (CSC) of the electrodes was calculated at the same time interval as the current during the second cycle of the voltage sweep and was normalized with respect to GSA.

Figure 12:
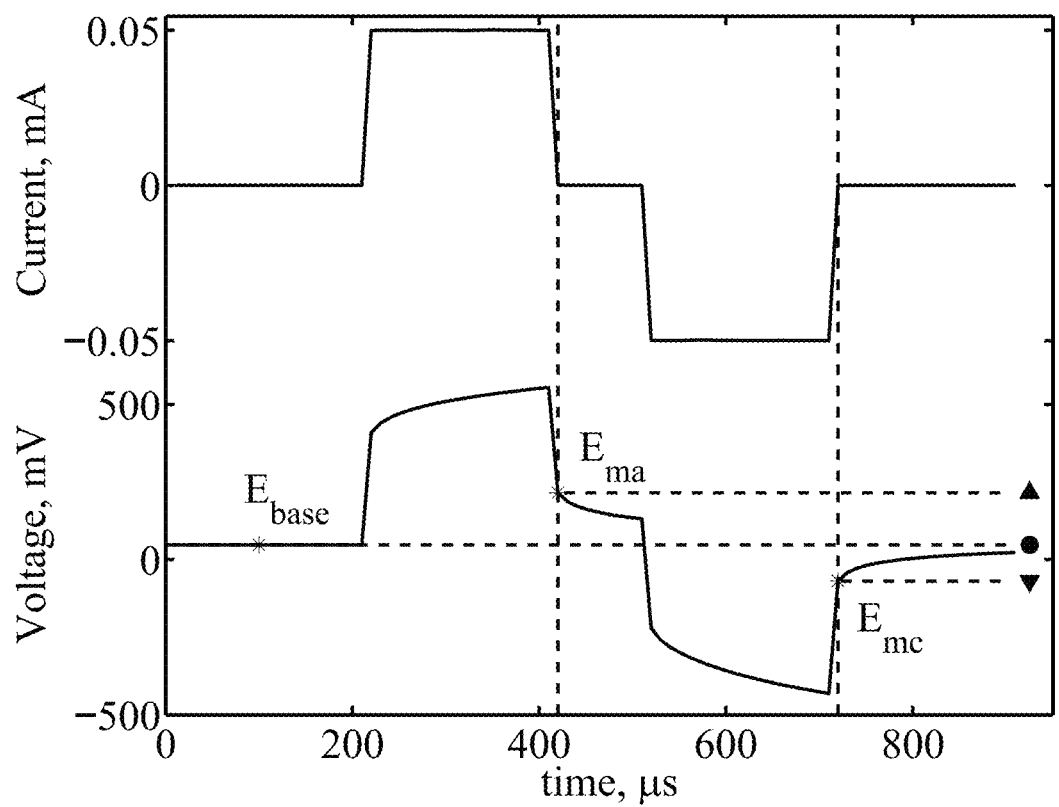
FIG. 12 is a plot of voltage transient and current waveform versus time for a microwire micro-reaction chamber electrode in phosphate buffered saline (PBS) during pulse stimulation, with definition of the anodic, cathodic, and base electrode polarization voltages $E_{ma}$, $E_{mc}$, $E_{base}$ used to determine maximal safe stimulation limits.

In vitro charge injection limit $Q_{inj}$ under pulse stimulation was measured using the methodology describe, for example by Cogan (Cogan, S. F. (2008). Neural stimulation and recording electrodes. *Annual review of biomedical engineering*, 10, 275-309. doi:10.1146/annurev.bioeng.10.061807.160518), defined from the maximum charge density that could be applied without the electrode potential exceeding the water window (–0.6 V and 0.8 V vs Ag/AgCl). As illustrated in FIG. 12, anodal-first biphasic charge-balanced current pulses are applied with symmetric cathodal and anodal pulse widths of 0.2 ms/phase and an interphase delay of 0.1 ms at 50 Hz in PBS using a constant-current stimulator between the test electrode and a large surface area 316L stainless steel current-return electrode and monitor the potential transient against a Ag/AgCl reference electrode. The interphase delay of 0.1 ms is introduced to disregard the access voltage resulting from the solution resistance. The potential measured at the starting of the interphase delay ($E_{ma}$) is a measure of the electrode polarization required to support the charge injection in the anodic leading phase. Similarly $E_{mc}$ is a measure of electrode polarization in the cathodic direction. The amount of charge injected in the leading phase of the pulse is the product of pulse amplitude and pulse width. We track the electrode polarization through $E_{ma}$ and $E_{mc}$ voltages for increasing values of injected charge. $Q_{inj}$ is the maximum charge density (charge injected divided by the GSA of the electrode) injected before either $E_{ma}$ crosses the positive threshold of 0.8 V or $E_{mc}$ crosses the negative threshold of –0.6 V. As previously indicated, the microwire µRC electrode pulse stimulation performance increases as a function of chamber size. Shown in FIGS. 13(a)-(c) are the electrode polarizations for increasing pulse amplitude for EIROF coated SPl electrode (see FIG. 13(a)) and µRC electrodes at 5 minute (see FIG. 13(b)) and 10 minute (see FIG. 13(c)) electrodissolution durations. The charge limits corresponding to the polarization crossing the thresholds of water electrolysis window for each electrode is marked by the vertical dashed line. For the SPl electrode the polarization crosses the –0.6 V limit for pulse amplitude of 0.11 mA. Hence the $Q_{inj}$ limit for this electrode is 1.02 mC/cm2. Whereas the limit for the micro-reaction chamber electrode for an etch duration of 5 minutes is 2.04 mC/cm$^2$ and for the substrate with etch duration of 10 min is 3.06 mC/cm$^2$.

Microwire Microelectrode Example

SEM micrographs of the electrodes after each state of the fabrication step are shown in FIGS. 3(a)-(c). Electrodissolution in hot sulphuric-phosphoric acid mixture resulted in selective dissolution of the active 316L stainless steel leaving behind a hollow noble metal (gold) tube that is insulated with polyimide from the outside. By adjusting the duration of the electrodissolution step, the depth of the micro-reaction chamber can be controlled. Selection of proper insulation material is critical, as the insulation material must be able to survive exposure to both the neural tissue environment and the electrodissolution solutions. Polyimide insulation is used for example in an exemplary aspect of the present invention.

Figure 9:
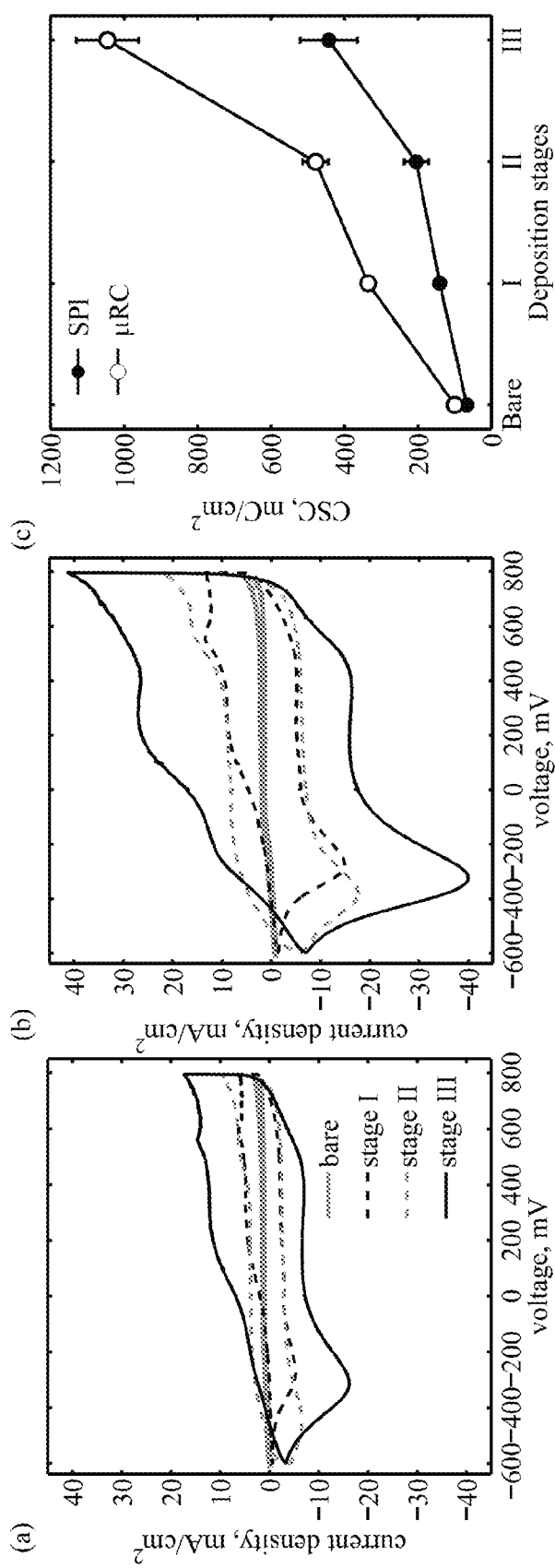
FIG. 9(a) is a plot of current versus voltage for a solid-planar (SPl) electrode shown as a function of the various stages of deposition.
FIG. 9(b) is a plot of current versus voltage for a microwire micro-reaction chamber electrode of the present invention shown as a function of the various stages of deposition.
FIG. 9(c) is a plot of charge storage capacity (CSC) as a function of the various stages of deposition comparing the microwire micro-reaction chamber electrode of the present invention to the SPl electrode.

Charge Storage capacity as measured by cyclic voltammetry for microwire electrodes formed from 50 µm diameter wire stock are shown in FIGS. 9(a)-(c). The cyclic voltammograms are shown as a function of the deposition stage for a three layer stack electroactive coatings. Specifically, in FIG. 9(a) and FIG. 9(b) the average current vs. voltage (CVs) of the SPl (see FIG. 9(a)) and μRC (see FIG. 9(b)) electrodes (n=5 each) after different stages of deposition of the 3 layer stack coatings comprising iridium oxide, conductive polymer and then iridium oxide are illustrated. Similar shapes of the curves represent similar charge transfer reactions on both SPl and microwire μRC electrodes. Both the areas enclosed by the microwire μRC electrodes CV curves are significantly larger than those of the SPl electrodes. Corresponding CSC values for the SPl and μRC electrodes are shown in FIG. 9(c). A corresponding factor of ~2.3 times improvement in CSC is observed for microwire μRC electrodes over the reference electrodes after each stage of stack coating deposition.

Figure 11:
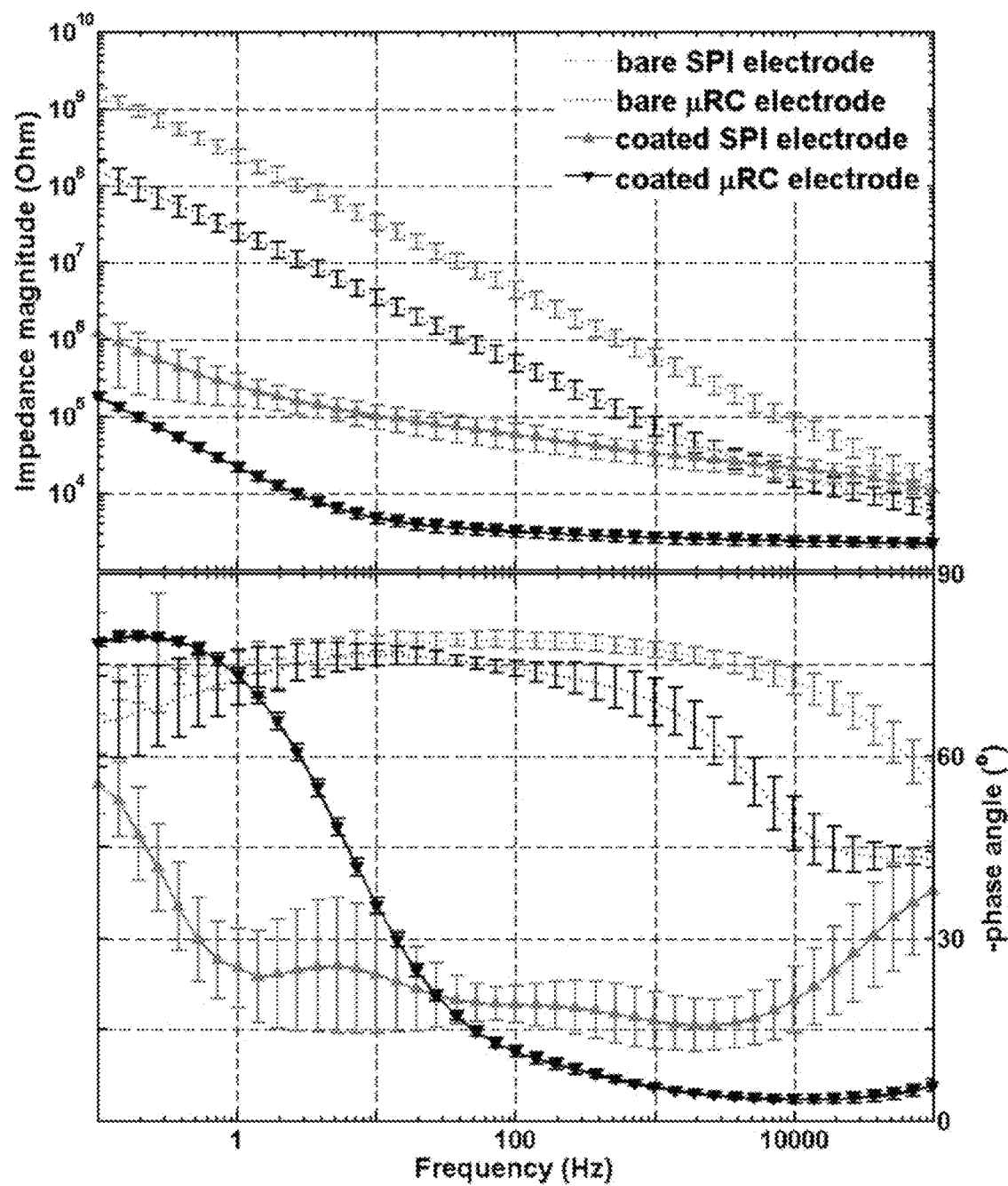
FIG. 11 shows a pair of plots for impedance magnitude (upper) and phase (lower) versus frequency for embodiments of various electrodes of the present invention.

Impedance plots of the different microwire electrodes tested are presented in FIG. 11. The μRC electrodes (without coatings) demonstrated one order of magnitude lower impedance as compared to that of the bare reference SPl electrodes for frequencies below 10 kHz. The addition of three-layered stack coatings significantly reduced the impedance of both the reference SPl and μRC electrodes of the present invention.

Further analysis of the plots indicates that the μRC impedance flattens out at about 10 Hz, indicative that the measure is dominated by the solution impedance and not the interference impedance. This interpretation is supported by the measured phase dependence, which crosses over from nearly 90° at low frequencies to nearly 0° by about 20 Hz. The phase behavior for the coated reference SPl is far less clear in interpretation.

Figure 10:
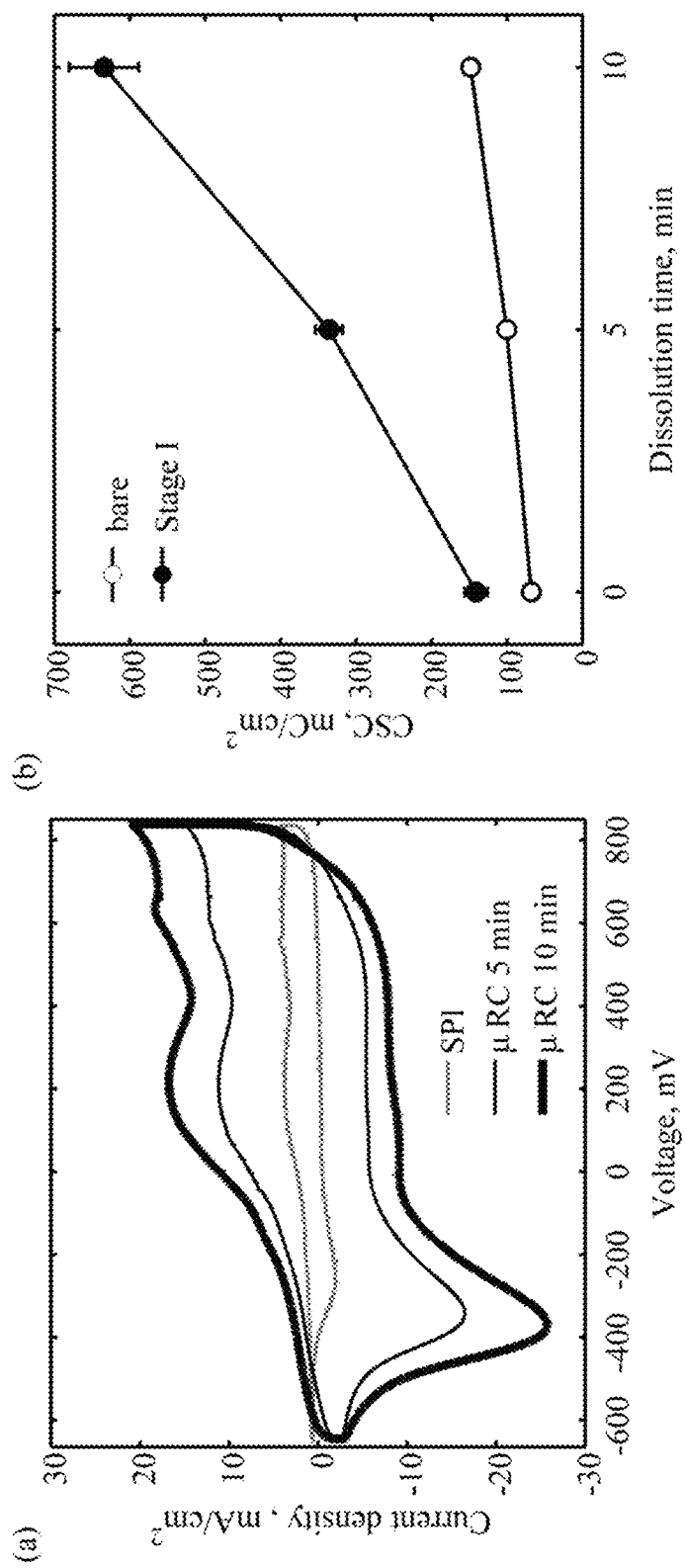
FIG. 10(a) is a plot of current versus voltage for as a function of increasing dissolution time comparing the microwire micro-reaction chamber electrode of the present invention to the SPl electrode coated with EIROF (iridium oxide).
FIG. 10(b) is a plot of charge storage capacity (CSC) as a function of increasing dissolution time comparing the microwire micro-reaction chamber electrode of the present invention to the SPl electrode.

Charge passing capacity is also a function of the volume of the reaction chamber. Chamber depth can be controlled in the microwire fabrication through for example the dissolution time, with longer dissolution time providing a deeper well and larger volume. Cyclic Voltammograms and CSCs for microwire electrodes with different dissolution times are presented in FIGS. 10(a)-(b), with zero dissolution time corresponding to SPl electrodes. As shown, CSC increases with chamber depth. It should be noted that deposition protocol of electroactive materials, such as the iridium oxide used here, needs to be altered for deeper chambers to ensure uniform coating on the electrochemical transfer interface (ETI).

Micro-reaction chamber electrodes with improved in vitro electrochemical characteristics are prepared from microwire electrodes. The coated microwire μRC showed about three orders of magnitude higher charge storage capacity than a bare solid-planar (SPl) electrode. Thus, for a given GSA of the electrode, the μRC electrodes can pass significantly higher amount of charge. In other words, μRC electrodes with smaller GSA can replace any counterpart with a higher GSA. Thus, μRC electrodes can help reduce the tissue trauma and increase the selectivity.

Both high frequency (~1 kHz) action potential recordings and lower frequency content (<300 Hz) local field potential (LFP) recordings provide useful information on the state and activity of the brain. Hence, lower impedance magnitude at 1 kHz and lower frequencies of μRC electrodes increase the signal-noise ratio of both action potential and LFP recordings.

Micro-reaction chamber electrodes also provide greatly improved charge injection under conditions used for pulse stimulation. Electrode polarization during pulse stimulation with anodic first biphasic charge-balanced symmetric pulses 0.2 ms/phase 0.1 ms inter-phase interval applied at 50 pulses/s is presented in FIGS. 10(a)-(b) for EIROF coated microwire electrodes with three different μRC dissolution times. SPl microwire electrodes (at zero dissolution time) reach unsafe electrode polarization at the lowest stimulation amplitude. The creation of a micro-reaction chamber greatly improves on this performance, with nearly a threefold improvement over the bare electrode being observed within the 10 minute dissolution time. As shown, longer duration etching increases the charge storage capacity of the electrodes. Increasing the duration of electrodissolution results in deeper micro-reaction chambers. This provides higher surface area for the electrochemical transfer interface (ETI) for a given GSA and hence supports higher charge transfer.

Notably, the ability to excite action potential from pulse stimulation is limited by the current amplitude of the applied pulse, which is in turn limited by the safety. Hence, improved charge injection capacity under pulse stimulation increases the ability to interact with brain.

The developed methodology for fabricating microwire based μRCs can directly be extended to batch production in multi-electrode bundles.

The utility of the present invention is not limited to electrical measurement and stimulation in biological tissue. The utility of the present invention is generally for making highly localized low-impedance connections with ionic conductive systems or features within an ionic environment, where one would like to either or measure potentials and/or pass current from a geometrically localized position. Such examples might be for measurement of electrochemical potentials or monitoring chemical species or applying current at localized positions within a larger reaction chamber. The advantages are the same in these cases as with interfacing with biological tissue.

Although specific materials and configurations are mentioned above for the manufacture and production of various features/components relating to the multi-reaction chamber electrodes, the present invention contemplates the use of other like materials exhibiting like characteristics. For example, the present invention contemplates that the conductive tube material is generally a material that has lower chemical reactivity in the given electrolyte than the active core metal. The conductive tube material possesses a good biocompatibility for use as a neuroelectrode. The conductive tube material is also generally capable of withstanding the harsh electropolishing and neurotissue environment. Examples of conductive tubing or conductive element to form the tube could be gold, or another non-reactive (or minimally reactive) metal or non-metal conductor, including platinum, iridium, conductive polymer, conductive composite materials, carbon fiber, carbon nanotubes (CNT), etc. The present invention also contemplates various materials for uses as an insulator or an insulating layer for the micro-reaction chamber microelectrode. In general, the insulation should bond well to the conductive tube material and have a high dielectric constant. The insulation should withstand harsh electropolishing and be compatible with neurotissue. In one exemplary embodiment of the present invention, polyimide is used as the insulating layer. Other insulators, such as parylene, may be used as an insulator. In one aspect of the present invention, the active core metal is stainless steel. Other active core materials are contemplated. The core material provides rigidity to the whole structure. The core material is preferably anodic to the tube material so it will undergo preferential dissolution in the sulphuric-phosphoric acid mixture. The active core material also possesses good corrosion resistance and biocompatibility. The electroactive coatings, according to one aspect of the present invention, include iridium oxide and conductive polymers. Other coatings are also contemplated. The electroactive coating should be biocompatible and stable, and capable of passing more charge across the electrode-tissue interface. The electrochemical changes the electroactive coating undergoes when applying an electrical signal should also be reversible. Additionally, the polymer network, such as a hydrogel, should be biocompatible and stable in brain tissue environment or in another ionic environment. The present invention contemplates sodium alginate hydrogel as one possible polymer network for providing sufficient porosity for ionic solution/fluid to flow or diffuse through the polymer network. Other polymer networks are also contemplated herein. In one aspect of the invention, the polymer network, such as hydrogel, serves as a mechanical buffer between the soft tissue and the hard/stiff electrode. In addition, the polymer network can serve as a structure or scaffold for the growth of conductive polymers or other materials added to increase electrochemical charge transfer. The result is a highly porous—or maybe skeletal—conductive structure configured in combination with a micro-reaction chamber.

The above Specification, examples, and data provide a complete description of the manufacture and use of the composition of the invention. Since many embodiments of the invention can be made without departing from the spirit and scope of the invention, the invention resides in the claims hereinafter appended.

What is claimed is:

1. A method for manufacture of micro-reaction chamber electrodes, comprising:
   providing an at least partially hollow chamber having a volume and terminating in an opening and having a high electrochemical transfer interface area to geometric surface area of the opening ratio, said at least partially hollow chamber formed at least in part within a portion of an electronic conductor wherein the electronic conductor forms one or more walls of the at least partially hollow chamber;
   distributing an electrochemical transfer interface throughout the at least partially hollow chamber to maximize surface area of the electrochemical transfer interface with respect to the at least partially hollow chamber; and
   providing a conductor in charge carrying communication with the at least partially hollow chamber via the electrochemical transfer interface.

2. The method of claim 1 wherein the electrochemical transfer interface comprises a coating of one or more electroactive species.

3. The method of claim 1 further comprising extending the electrochemical transfer interface into the at least partially hollow chamber by one or more conductive threads or fibers.

4. The method of claim 1 further comprising extending the electrochemical transfer interface into the at least partially hollow chamber by a conductive mesh or scaffolding.

5. The method of claim 1 further comprising extending the electrochemical transfer interface into the at least partially hollow chamber by depositing through a polymer.

6. A micro-reaction chamber electrode comprising:
   an at least partially hollow chamber having a volume and terminating in an opening, wherein the at least partially hollow chamber is configured to increase an electrochemical transfer interface area relative to a geometric surface area of the opening, said at least partially hollow chamber formed at least in part within a portion of an electronic conductor wherein the electronic conductor forms one or more walls of the at least partially hollow chamber; and
   an electrochemical transfer interface distributed throughout the at least partially hollow chamber to maximize surface area of the electrochemical transfer interface with respect to the at least partially hollow chamber volume; and
   a conductor in charge carrying communication with the at least partially hollow chamber via the electrochemical transfer interface;
   wherein the electrochemical transfer interface of the at least partially hollow chamber is configured to be larger than an electrochemical transfer interface of an equivalent-sized solid planar electrode.

7. The micro-reaction chamber electrode of claim 6 further comprising an electroactive species covering the surface of the at least partially hollow chamber to increase its charge passing capacity.

8. The micro-reaction chamber electrode of claim 6 further comprising a conductor extending into the at least partially hollow chamber to extend the electrochemical transfer interface.

9. The micro-reaction chamber electrode of claim 6 further comprising one or more polymers within the at least partially hollow chamber.

10. The micro-reaction chamber electrode of claim 6 wherein the minimal distance from the opening of the at least partially hollow chamber to an inner conductive wall and the electrochemical transfer interface is substantially smaller than the opening.

11. The micro-reaction chamber electrode of claim 7 wherein the electroactive species comprises iridium oxide.

12. The micro-reaction chamber electrode of claim 6 further comprising an insulating layer at least partially enclosing the electrochemical transfer interface.

13. The micro-reaction chamber electrode of claim 12 wherein the insulating layer comprises polyimide.

14. The micro-reaction chamber electrode of claim 6 further comprising a core material removed to form the at least partially hollow chamber.

15. The micro-reaction chamber electrode of claim 14 wherein the conductor has a lower chemical reactivity than the core material in an ionic conductive environment.

16. The micro-reaction chamber electrode of claim 6 wherein the electrochemical transfer interface is distributed throughout the at least partially hollow chamber volume to reduce the access resistance from the electrochemical transfer interface to the opening.

17. A method for manufacturing micro-reaction chamber electrodes, comprising:
   providing a hollow chamber having a volume and terminating in an opening, wherein the hollow chamber comprises a high surface area to volume ratio, said hollow chamber formed at least in part within a portion of an electronic conductor wherein the electronic conductor forms one or more walls of the hollow chamber;
   distributing an electrochemical transfer interface throughout the hollow chamber to maximize surface area of the electrochemical transfer interface with respect to the hollow chamber volume;
   coating the electrochemical transfer interface with one or more electroactive species; and
   providing a conductor in charge carrying communication with the hollow chamber via the electrochemical transfer interface.

18. The method of claim 17 wherein the opening terminates in an electrode-tissue interface.

19. The method of claim 17 further comprising partially enclosing the electrochemical transfer interface with an insulating layer.

20. The method of claim 18 further comprising spatially separating the electrode-tissue interface from the electrochemical transfer interface with the hollow chamber for increasing charge storage capacity and decreasing impedance.

21. The method of claim 17 wherein the one or more electroactive species comprise iridium oxide.

22. The method of claim 17 further comprising one or more polymers within the hollow chamber.

* * * * *